United States Patent
Kozloski et al.

(10) Patent No.: US 10,264,972 B2
(45) Date of Patent: Apr. 23, 2019

(54) DISPENSING DRUGS FROM A COMPANION DIAGNOSTIC LINKED SMART PILL

(75) Inventors: James R. Kozloski, New Fairfield, CT (US); Clifford A. Pickover, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 818 days.

(21) Appl. No.: 13/476,147

(22) Filed: May 21, 2012

(65) Prior Publication Data

US 2013/0310663 A1    Nov. 21, 2013

(51) Int. Cl.
| | |
|---|---|
| *A61B 5/07* | (2006.01) |
| *A61B 5/00* | (2006.01) |
| *A61M 31/00* | (2006.01) |
| *A61B 5/145* | (2006.01) |

(52) U.S. Cl.
CPC ............ *A61B 5/0031* (2013.01); *A61B 5/073* (2013.01); *A61M 31/00* (2013.01); *A61B 5/07* (2013.01); *A61B 5/14539* (2013.01); *A61B 5/6861* (2013.01); *A61B 2562/162* (2013.01)

(58) Field of Classification Search
CPC ..... A61B 5/07; A61B 5/14539; A61B 5/6861; A61B 2562/162
USPC ....................................................... 600/302
See application file for complete search history.

(56) References Cited

U.S. PATENT DOCUMENTS

| | | | |
|---|---|---|---|
| 5,318,557 A | 6/1994 | Gross | |
| 5,792,048 A | 8/1998 | Schaefer | |
| 6,929,636 B1 | 8/2005 | Von Alten | |
| 7,226,442 B2 | 6/2007 | Sheppard et al. | |
| 7,817,030 B2 | 10/2010 | Hood et al. | |
| 8,036,748 B2 | 10/2011 | Zdeblick et al. | |
| 2002/0055734 A1* | 5/2002 | Houzego | A61M 25/01 604/891.1 |
| 2004/0092825 A1* | 5/2004 | Madar | A61B 1/041 600/473 |
| 2005/0100937 A1* | 5/2005 | Holmes | A61B 5/0024 435/6.12 |
| 2005/0148847 A1* | 7/2005 | Uchiyama et al. | 600/407 |

(Continued)

FOREIGN PATENT DOCUMENTS

| | | |
|---|---|---|
| CN | 1777389 A | 5/2006 |
| CN | 1856290 A | 11/2006 |

(Continued)

OTHER PUBLICATIONS

Rolfe C. Anderson, et al., "A Miniature Integrated Device for Automated Multistep Genetic Assays," 2000 Oxford University Press, Nucleic Acids Research, 2000, vol. 28, No. 12, Apr. 2000, 6 pages.

(Continued)

*Primary Examiner* — Puya Agahi

(74) *Attorney, Agent, or Firm* — Cantor Colburn LLP; Vazken Alexanian

(57) ABSTRACT

A mechanism is provided. The mechanism includes a user device and a smart pill within a host. The smart pill is communicatively connected to the user device for transmitting and receiving secure communications. Settings of the smart pill while in the host are configured to be changed based on patient category data of the host.

11 Claims, 9 Drawing Sheets

(56) References Cited

U.S. PATENT DOCUMENTS

| | | | |
|---|---|---|---|
| 2006/0115323 A1* | 6/2006 | Coppeta | A61K 9/0097 |
| | | | 403/270 |
| 2006/0259328 A1 | 12/2006 | Burd et al. | |
| 2008/0112885 A1 | 5/2008 | Okunev et al. | |
| 2008/0146871 A1* | 6/2008 | Arneson et al. | 600/101 |
| 2009/0182207 A1* | 7/2009 | Riskey et al. | 600/302 |
| 2009/0256702 A1 | 10/2009 | Robertson et al. | |
| 2009/0306633 A1* | 12/2009 | Trovato | A61B 1/041 |
| | | | 604/891.1 |
| 2010/0130836 A1* | 5/2010 | Malchano | A61B 1/05 |
| | | | 600/301 |
| 2010/0130837 A1 | 5/2010 | Matott | |
| 2010/0185055 A1* | 7/2010 | Robertson | A61B 5/0031 |
| | | | 600/117 |
| 2010/0280842 A1* | 11/2010 | Iwase | G06F 19/321 |
| | | | 705/2 |
| 2011/0017612 A1* | 1/2011 | Dijksman et al. | 205/799 |
| 2011/0092959 A1* | 4/2011 | Zou et al. | 604/890.1 |
| 2011/0160699 A1 | 6/2011 | Imran | |
| 2011/0166416 A1* | 7/2011 | Katayama | A61B 1/00082 |
| | | | 600/104 |
| 2011/0275410 A1* | 11/2011 | Caffey | A61M 5/14526 |
| | | | 455/557 |

FOREIGN PATENT DOCUMENTS

| | | | |
|---|---|---|---|
| CN | 101259301 A | 9/2008 | |
| CN | 101286048 A | 10/2008 | |
| CN | 101352343 A | 1/2009 | |
| CN | 101472640 A | 7/2009 | |
| CN | 101541359 A | 9/2009 | |
| CN | 101945613 A | 1/2011 | |
| CN | 103025319 A | 4/2013 | |
| WO | 2008053393 A2 | 5/2008 | |
| WO | WO 2008053396 A2 * | 5/2008 | A61B 1/041 |

OTHER PUBLICATIONS

Krista Hessler Carver "Companion Diagnostics: Evelving FDA Regulation and Issues for Resolution," Internet: http://www.cov.com/files/Publication/e5c4b3dc-1832-4742-9937-84f965052b44/Presentation/PublicationAttachment/7795d260-621d-4d13-bd29-863acac00254/Companion%20Diagnostics%20-%20Evolving%20FDA%20Regulation%20and%20Issues%20for%20Resolution.pdf; May 14, 2010, 36 pages.

Anni Shaer Levitt "Philips' Smart Pill to Deliver Drugs," Internet: http://thefutureofthings.com/news/5810/philips-smart-pill-to-deliver-drugs.html; Nov. 21, 2008; 2 pages.

S. Maqbool et al., "Wireless Capsules Motility: Comparison of the SmartPill GI Monitoring System with Scintigraphy for Measuring Whole Gut Transit," Digestive Diseases and Sciences, vol. 54, No. 10, 2009, pp. 2167-2174.

C. McCaffrey et al., "Swallowable-Capsule Technology," IEEE Pervasive Computing, vol. 7, No. 1, Jan.-Mar. 2008, pp. 23-29.

Jeanene Swanson, "Companion Diagnostics Take Off," Internet: http://www.genomeweb.com/dxpgx/companion-diagnostics-take, OpGen, Genome Technology, MDx, Oct. 2009, 4 pages.

A. C. Tikka et al., "Secure Wireless Powering and Interrogation of an Implantable Microvalve," 2011 IEEE Topical Conference on Biomedical Wireless Technologies, Networks, and Sensing Systems (BioWireleSS), Jan. 16-19, 2011, pp. 35-38.

Roey Tzezana "Micro-Origami—Tiny Packages for Drug Delivery," Internet: http://thefutureofthings.com/news/1193/micro-origami-tiny-packages-for-drug-delivery.html; May 30, 2008; 2 pages.

\* cited by examiner

DISPENSING DRUGS FROM A COMPANION DIAGNOSTIC LINKED SMART PILL

BACKGROUND

The present invention relates generally to smart pills, and more specifically, to companion diagnostics communicatively linked to the smart pill.

Swallowable capsules (also referred to as smart pills) have been evolving for almost half a century and are now helping uncover gastrointestinal (GI) tract mysteries in diagnostic and therapeutic applications. Additional information about swallowable capsule technology is found in "Swallowable-Capsule Technology" by Colm McCaffrey, Olivier Chevalerias, Cian O'Mathuna, and Karen Twomey, published by IEEE CS 1536-1268/08© 2008 IEEE, which is herein incorporated by reference in its entirety.

In general, a swallowable capsule is a self-contained microsystem that performs a sensing or actuating function in the body. Usually, the system consists of the core components, such as sensors, signal conditioning, a power supply, central processing unit (CPU), and communication, encapsulated in a biocompatible material.

At one end of the chain are the sensors (or alternatively, actuators) that interface with the body. Sensors convert physical properties such as light, pressure, or temperature into electrical signals, while actuators perform the opposite function. The signal-conditioning block provides analog processing such as amplification and filtering to "clean" the detected signal. The system's brain, the CPU, digitizes the signal and might perform additional processing. The communication block can then transmit the signal to a receiver module outside the body.

The communication medium can be radio frequency (RF), a magnetic field (inductive coupling), or ultrasound. Finally, the power supply, based on either batteries or inductive coupling, provides energy for the system.

An article entitled "Philips' Smart Pill to Deliver Drugs" (Nov. 21, 2008) by Anni Shaer Levitt is herein incorporated by reference in its entirety. Philips' research division has developed a miniature pill that can administer drugs directly to specific places in the digestive tract. The new technology, named "iPill", might enable new therapies for life-threatening disorders such as Crohn's disease, colitis, and colon cancer, along with assisting in the development of new drugs. Camera pills have come a long way since the first one was approved by the Federal Drug Administration (FDA) for diagnostic applications in 2000; ever since, most smart pills have been developed for this purpose only. Now, Philips is aiming to change this approach by developing a pill which can also take an active role in therapy. The iPill is a tiny capsule, similar to a camera pill, which was designed to be swallowed and then to pass through the digestive tract. Before the intake, it can be programmed to deliver medicine in a controlled fashion according to a pre-defined drug release profile which is to be created per patient and condition, and it is focused on treating conditions in different areas of the intestine. The iPill combines electronics with diagnostic and therapeutic properties in hopes of targeting almost any kind of drug to a specific location in the intestinal tract.

The device can determine its precise location in the intestinal tract by measuring the acidity of its surroundings. Different areas of the intestinal tract have specific pH values (the common measure for acidity). The stomach is highly acidic but the acidity drops dramatically right after the exit toward the intestine and continues to drop from the upper intestine onwards. Using these measures in combination with the data on the pill's transit times, the location can be easily determined. In addition, the pill measures the local temperature and reports measurements to an external receiver unit. When the iPill reaches an area defined in its drug-release profile, it begins accurately releasing the drug from the reservoirs using a microprocessor controlled pump.

SUMMARY

According to an embodiment, a system is provided. The system includes a user device and a smart pill configured to be swallowed by a host. The smart pill is communicatively connected to the user device for transmitting and receiving secure communications. Settings of the smart pill for the host are configured to be changed automatically based on relayed patient category data of the host, diagnostic data of the host collected by the smart pill, and a relayed program that takes the patient category data and the diagnostic data as inputs.

According to an embodiment, a smart pill configured to be swallowed by a host is provided. The smart pill includes a controller, a dispenser, and a reservoir housing a drug. The controller is configured to receive patient category data while in the host. Settings of the smart pill for the host are configured to be changed automatically based on relayed patient category data of the host, diagnostic data of the host collected by the smart pill, and a relayed program that takes the patient category data and the diagnostic data as inputs.

According to an embodiment, a method for a smart pill is provided. The method includes communicatively connecting the smart pill to the user device for transmitting and receiving secure communications, while the smart pill is in a host. The method includes changing settings of the smart pill for the host automatically based on relayed patient category data of the host, diagnostic data of the host collected by the smart pill, and a relayed program that takes patient category data and the diagnostic data as inputs According to an embodiment, a method for a smart pill configured to be swallowed by a host is provided. The method includes configuring the smart pill with a controller, a dispenser, and a reservoir housing a drug. The controller receives patient category data while in the host. Settings of the smart pill while in the host are configured to be changed automatically based on the patient category data of the host, diagnostic data of the host collected by the smart pill, and a relayed program that takes the patient category data and the diagnostic data as inputs Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
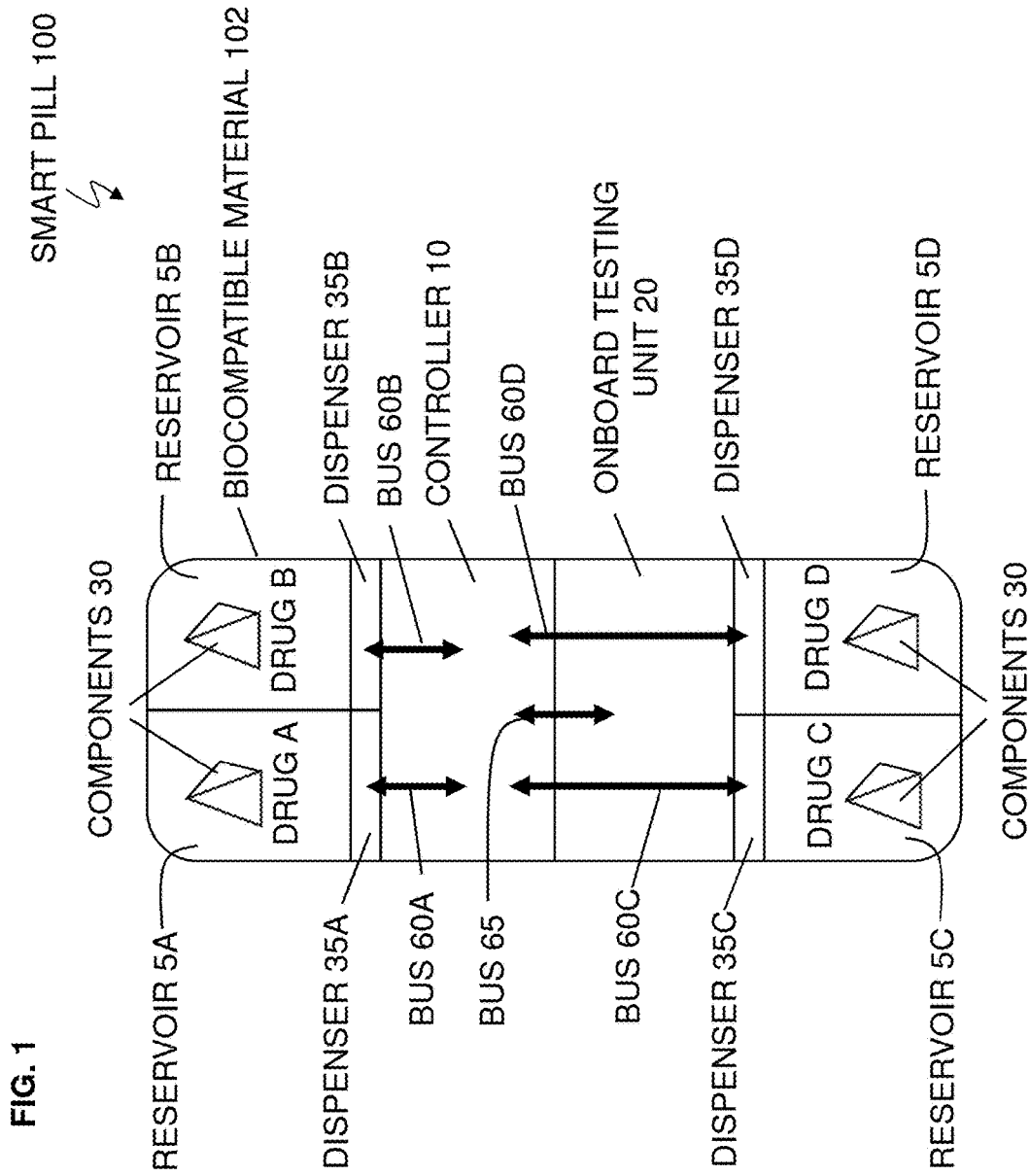
FIG. 1 illustrates a smart pill according to an embodiment.

Embodiments provide a mechanism that employs a small device (e.g., smart pill) that includes companion diagnostics (e.g., such as but not limited to genetic, biochemical, and/or visual tests along with resulting companion diagnostics data), and based on such tests (of the companion diagnostics), provide a signal to a treatment controller (i.e., control unit) in order to provide real-time personalization of medical treatment, automatically tailored for a subset of a population.

As sophisticated tests have become more rapid and miniaturized, including genetic tests, the present disclosure provides increased utility for medical providers, drug companies, and patients.

Embodiments disclose a mechanism for monitoring body characteristics (e.g., disease states, biomarkers, etc.) using a handheld unit (such as a smart phone) with an interface to a disease state and/or biomarker database. The embodiments convey the disease and/or biomarker information to a healthcare professional, enabling a change of the smart pill characteristics (and energy use by the smart pill) to improve drug delivery, ensure safety, and continued operation on the smart pill with limited supplies of power if in use for many days. The handheld unit also receives information on alternate treatments with potentially useful healing characteristics.

Companion diagnostic tests exist at the front lines of drug discovery and development and promise to change the way drugs are made and marketed. These tests of the companion diagnostic aim to identify, using analysis of genetic, proteomic, and/or gene expression biomarkers, certain subpopulations who respond better or who are likely to have an adverse effect to a particular drug. In the past, drug companies were not concerned with identifying such populations, because developing drugs that benefit the patient population as a whole and show adverse effects in only small subpopulations was significantly easier. Today, a dramatic decrease in drug approval rates and a dramatic increase in unrecovered costs in research and development have driven companies to seek approval for drugs with companion diagnostics.

Companion diagnostics are approved by regulators together with a drug to ensure that only the targeted subpopulation is administered the drug while others are avoided. While the overall market for each drug is therefore necessarily smaller, the percentage of drugs that may be approved with various companion diagnostics is larger. Research and development costs for each drug are therefore more readily offset, albeit resulting in a larger number of somewhat less profitable drugs. Indeed, some drugs that have already failed to gain acceptance in clinical trials may be "resuscitated" in the approval process by resubmitting them with a companion diagnostic.

Evidence for this trend comes from a recent action by the Food and Drug Administration (FDA) to change the labeling of certain colon cancer drugs to indicate suitability only for people with non-mutated forms of the KRAS gene. GTPase KRAS (also known as V-Ki-ras2) is Kirsten rat sarcoma viral oncogene homolog, and KRAS is a protein that in humans is encoded by the KRAS gene. Such a narrowing of the scope of a target population for a drug is (only) possible when a companion diagnostic is available to test for this genetic marker. In the absence of such a test, the drug would have likely been pulled from the market by the FDA.

Problems arise in the development, regulation, and marketing of drugs with their companion diagnostics for a variety of reasons. Testing drugs on genetically identified subpopulations is more costly, especially when a broad search must be conducted for the most effective biomarker-drug combination. Regulating drugs with their companion diagnostics requires new guidelines and methods of validating that the drug is effective for the subpopulation, and that the companion diagnostic is prescribed and administered correctly in the clinical setting together with the drug. Marketing drugs to only the subpopulation also means that broadcast methods of educating and advertising to both clinicians and patients may no longer be effective as the complexities of various drug-diagnostic combinations may be beyond the ability of patients and even doctors to comprehend and/or readily retain when communicated through traditional media and educational literature.

All of these problems derive from the specialization of drugs to targeted subpopulations, and the necessary fragmentation of the drug market that results. A solution to this problem is to continue to test, regulate, and market within the broader population a single- or multi-drug delivery device which is ingested or implanted, for example in the form of a smart pill (e.g., smart pill 100 in FIG. 1) according to an embodiment. The device (i.e., smart pill) may then be communicatively coupled to a companion diagnostic, allowing the smart pill to dispense an appropriate drug at the appropriate dose to the patient identified as part of a targeted subpopulation (e.g., patient categories 1, 2, 3 through N). In this way, testing, regulating, and marketing are no longer dependent on an externally and manually administered couplings between drugs and their companion diagnostics, but instead are logically associated and administered by a digital computerized system which can be programmed, upgraded, and modified in an on demand manner.

FIG. 1 depicts a smart pill (i.e., swallowable pill or device) 100 encapsulated in a biocompatible material 102 according to an embodiment. A biocompatible material (sometimes shortened to biomaterial or referred to as biomimetic material) is a synthetic or natural material used to replace part of a living system or to function in intimate contact with living tissue. Biocompatible materials are not made by living organisms but have compositions and properties similar to those made by living organisms. Surface functionalization may provide a way to transform a bio-inert material into a biomimetic or even bioactive material by coupling of protein layers to the surface, or coating the surface with self-assembling peptide scaffolds to lend bioactivity and/or cell attachment 3-D matrix. Different approaches to functionalization of biomaterials exist. Plasma processing can be applied to chemically inert materials like polymers or silicon to graft various functional groups to the surface of the smart pill 100. Particularly, polyanhydrides are polymers which have used as a drug delivery materials.

The smart pill 100 includes a controller 10, an onboard testing unit 20, dispensers 35A, 35B, 35C, and 35D, and reservoirs 5A, 5B, 5C, and 5D respectively housing components 30. The controller 10 individually controls and communicates with the respective dispensers 35A, 35B, 35C, and 35D via respective buses 60A, 60B, 60C, and 60D, which allows the controller 10 to dispense the components 30 into a patient (e.g., a human, animal, and/or any host) based on companion diagnostics. The components 30 may be drugs A, B, C, and D respectively housed in reservoirs 5A, 5B, 5C, and 5D.

Note that the components 30 may be and/or include one or more stem cells, viruses, parasite eggs, parasites, and/or bacteria. Although various scenarios discussed herein for the components 30 may be with respect to drugs, it is contemplated that components 30 are not meant to be limited to drugs. One or more of the stem cells, viruses (as sometimes viruses can be used therapeutically), parasite eggs (e.g., helminthic therapy can be used to mediate autoimmune response), parasites, and/or bacteria (e.g., to regulate favorable colonization in the stomach/intestines) may be in their own respective dispensers 35A, 35B, 35C, and 35D in addition to drugs A, B, C, D, as an alternative to drugs A, B, C, D, and/or as replacements (in a desired combination) to some of the drugs A, B, C, D.

In one case, the drugs A, B, C, and D may be different such that individual drugs can be combined into any dispensing combination (from respective reservoirs 5A, 5B, 5C, and 5D) as controlled by the controller 10. For example, drugs A and B may be dispensed by the controller 10 while drugs C and D are not dispensed, based on companion diagnostic data. Also, addition to drugs A, B, C, and D, the components 30 may be stem-cell set A versus (different) stem-cell set B, virus set A versus (different) virus set B, parasite eggs A versus (different) parasite eggs B, and bacterial set A versus (different) bacterial set B.

In another case, the drugs A, B, C, and D may be different quantities (i.e., dosages) of the same drug. For example, the dosage from highest to lowest is drug A (e.g., 4 mg or mL), then drug B (3 mg or mL), then drug C (2 mg or mL), and last drug D (1 mg or mL). Accordingly, the controller 10 can cause any dosage (in any combination) of the same drug based on companion diagnostic data. Also, if the maximum dosage is required (based on companion diagnostic data), the controller 10 can cause all of the dispensers 35A, 35B, 35C, and 35D to respectively dispense drugs A, B, C, and D in the patient.

The dispensers 35A, 35B, 35C, and 35D may generally be referred to as dispensers 35, and the buses 60A, 60B, 60C, and 60D may generally be referred to as buses 60. Likewise, reservoirs 5A, 5B, 5C, and 5D may generally be referred to as reservoirs 5.

Bus 65 allows the controller 10 to communicate with and control the onboard testing unit 20. By individually controlling dispensers 35A, 35B, 35C, and 35D, the controller 10 dispenses the drugs (components 30) based on companion diagnostics (i.e., results of tests) received from the onboard testing unit 20 and/or a handheld unit 250 (shown in FIG. 2). For example, the controller 10 is configured to determine the amount of components 30 (i.e., the dosage) to dispense to the patient, along with determining which particular components 30 to dispense to the patient (when more than one type of drug is housed in the different reservoirs 5). For example, the controller 10 is configured to determine the particular combination of components 30 (e.g., such as drug A, drug B, drug C, and/or drug D) that should be dispensed by the respective dispensers 35A, 35B, 35C, and 35D based on the companion diagnostics, and the controller 10 sends dispense signals to selected ones of the buses 60A-D while not to other. Based on the companion diagnostics, the controller 10 can determine that two drugs such as drugs A and B are to be dispensed to the patient while drugs C and D are not. Accordingly, the controller 10 causes the dispensers 35A and 35B (via buses 60A and 60B) to respectively open reservoirs 5A and 5B to dispense drugs A and B, while not dispensing drugs C and D. Moreover, the controller 10 can dispense any combination (including 1, 2, 3, 4, and/or none) of the drugs A, B, C, and D as desired via the individual buses 60A, 60B, 60C, and 60D, based on the companion diagnostics.

Figure 2:
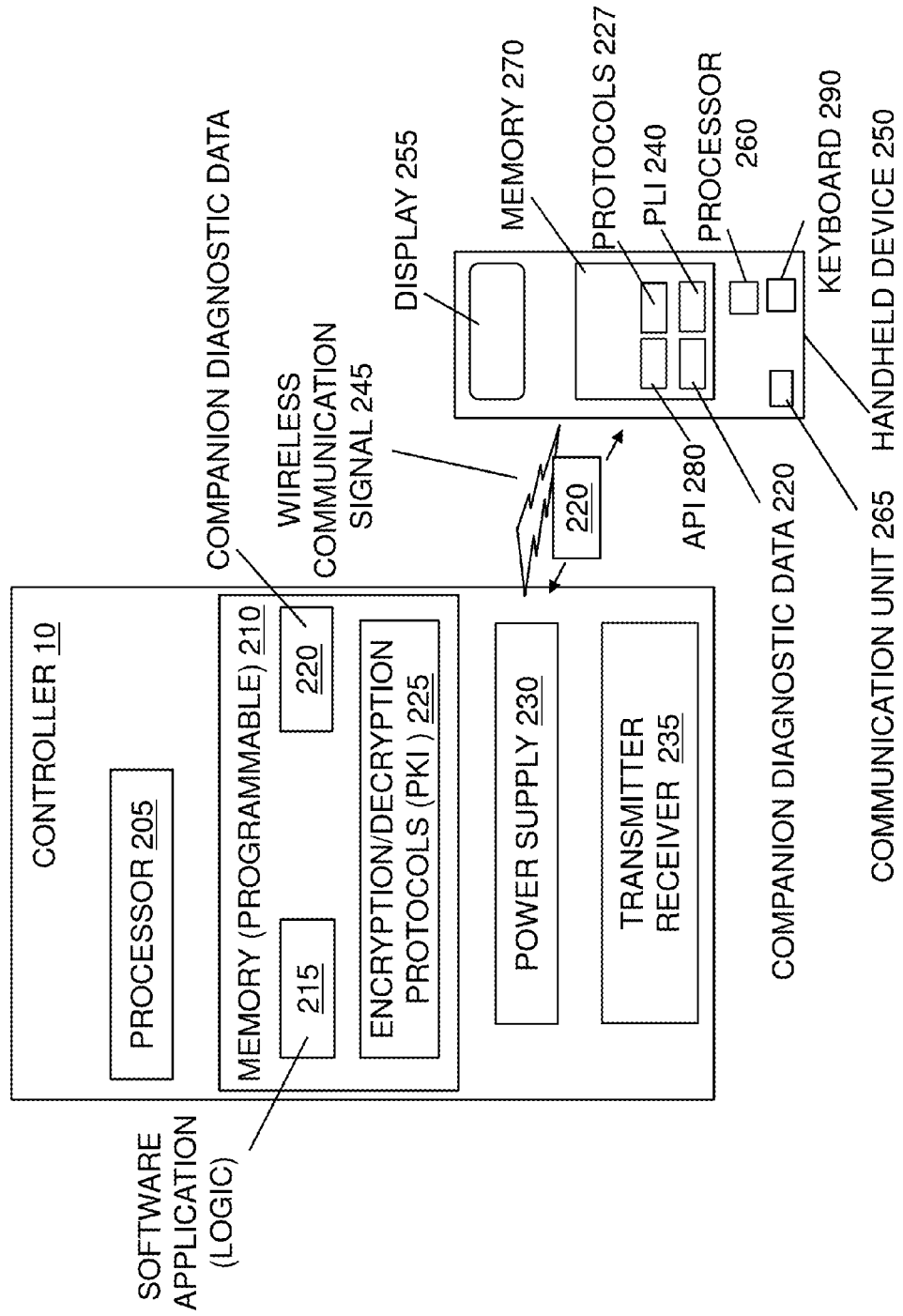
FIG. 2 illustrates details of a controller of the smart pill and a handheld device according to an embodiment.
Figure 3:
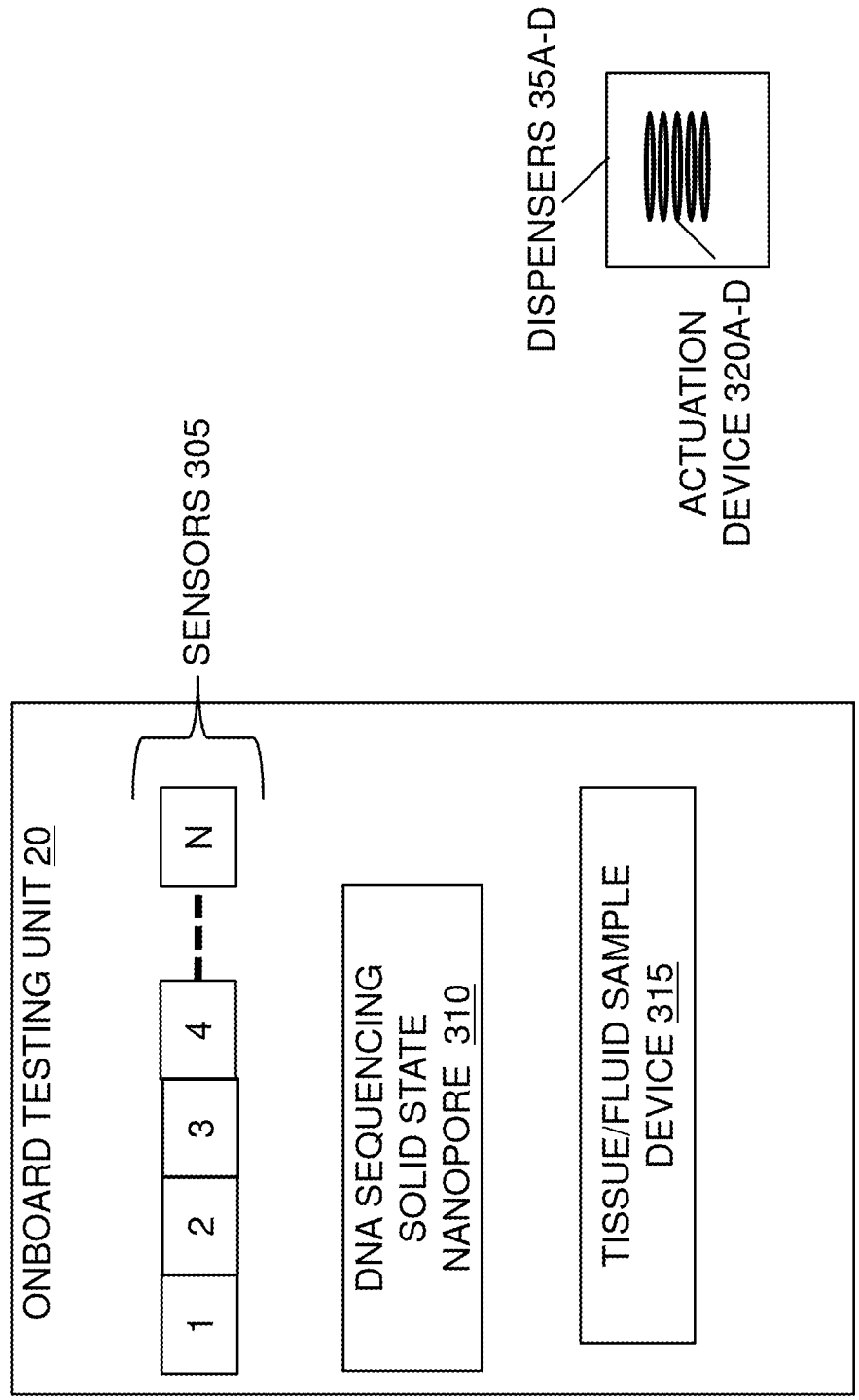
FIG. 3 illustrates details of an onboard testing unit of the smart pill according to an embodiment.

When all of the components 30 are the same (i.e., drugs A, B, C, and D are the same), the controller 10 can cause only certain dispensers 35 (e.g., drug A and B) to dispense components 30 and/or can cause all dispensers 35 to dispense components 30 to meet the correct dosage/amount as determined by the controller 10 based on the companion diagnostics. FIGS. 2 and 3 provide further details of the smart pill 100 and the handheld device 250 according to an embodiment.

FIG. 2 illustrates the controller 10 of the smart pill 100 with a processor 205 (e.g., a central processor unit), memory 210 (at least part of the memory 210 is programmable), software application (i.e., logic) 215 stored in the memory 210, companion diagnostic data 220 (corresponding to a particular patient category) stored in the memory 210, and encryption and decryption protocols (PKI) 225 for securely encoding and decoding communications. The controller 10 also includes a power supply 230 (which may be a battery and/or a coil/inductor system that is energized from an external device), and a transmitter and receiver communication unit 235 (including an antenna) for wirelessly transmitting and receiving communication signals 245. FIG. 2 also illustrates the handheld device 250 which may include a display 255, a processor 260 (central processing unit), a programmable logical interface 240 (e.g., stored in memory 270) and a communication unit 265 (including a transmitter, receiver, and a network interface circuit) to communicate wireless communication signals 245.

In one scenario, the programmable logical interface 240 of the handheld device 250 (e.g., a smart cellphone) interprets a logical program provided by a drug development laboratory and/or a regulatory body, and the handheld device 250 relays the logic to the controller 10 inside the smart pill 100 via a transmitter/receiver communication unit 235. The controller 10 receives logic (which can be stored as software application (logic) 215 (which may be a binary program) to determine which components 30 and/or combination of components 30 to dispense, along with determining whether or not to dispense any components 30 (i.e., drugs A, B, C, and D) at all for this patient, based on the companion diagnostics data 220 (i.e., test results) for this particular patient. The controller 10 receives the results of tests, i.e., companion diagnostic data 220, which may be results of, e.g., genetic, proteomic, and/or gene expression tests, from the onboard testing unit 20 (i.e., the companion diagnostic component in the smart pill 100 itself) and/or from the handheld device 250. The controller 10 evaluates the test results (companion diagnostic data 220 corresponding to a particular patient category) given the loaded software application (program) 215 and under appropriate conditions releases certain drugs (i.e., components 30) from the reservoirs 5 within the smart pill 100 as discussed herein.

Figure 4:
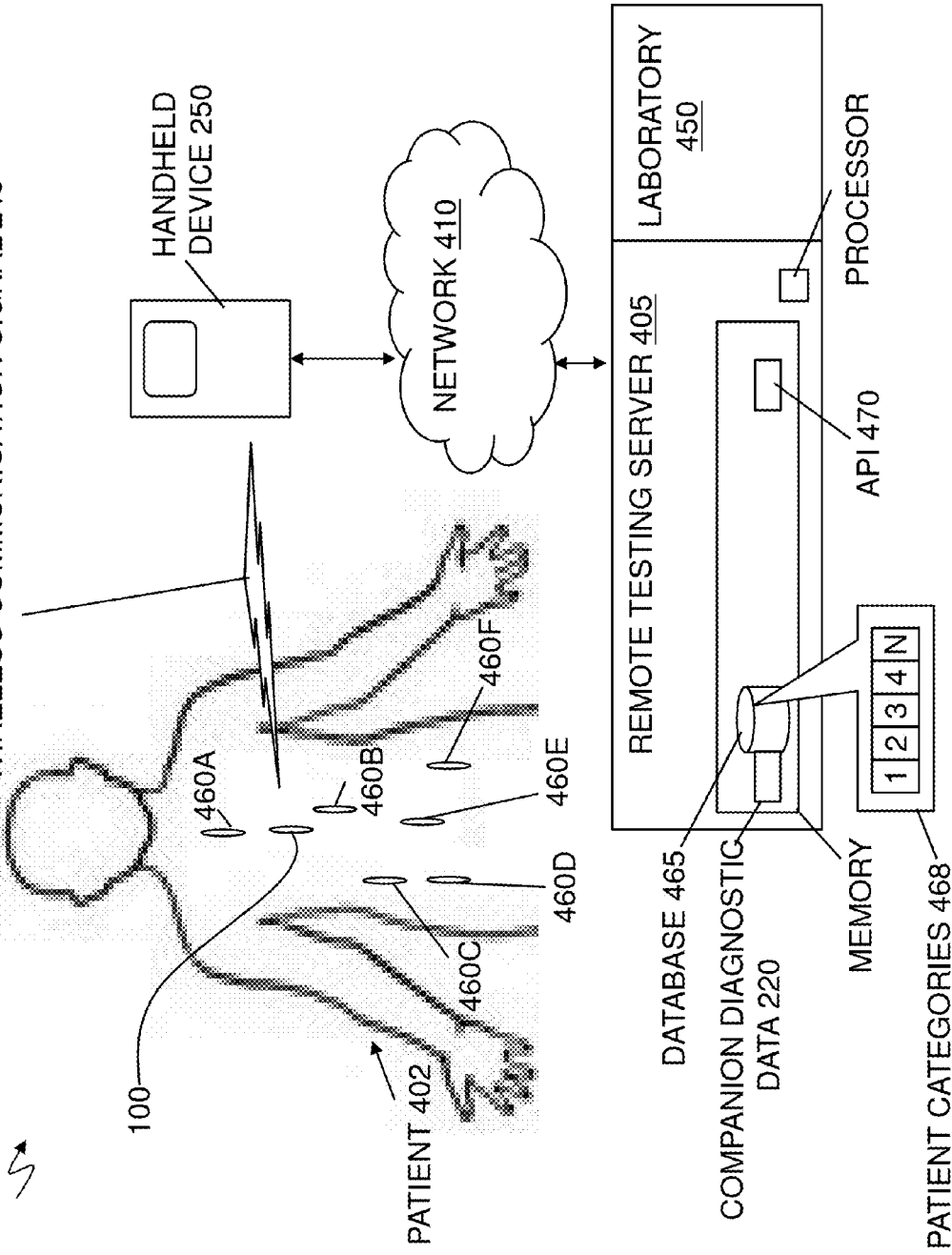
FIG. 4 illustrates a system according to an embodiment.

In one implementation, the onboard testing unit 20 (i.e., companion diagnostic component) may be external to the smart pill 100, either implanted in a different place in the body of the patient and/or external to the patient (e.g., in the handheld device 250, a remote testing server 405 (as shown in FIG. 4), etc. If external, the companion diagnostic data 220 (in whole or part) which can be communicated to the smart pill 100 via the handheld device 250).

Security concerns prompt the use of a secure protocol for information exchange, such as the encryption and decryption protocols (PKI) 225 which are implemented by both the software application (logic) 215 transmitting and receiving wireless communication signals 245 through the transmitter/receiver unit 235 and the encryption and decryption protocols (PKI) 227 implemented by the programmable logical interface 240 via the communication unit 265. PKI is a public key infrastructure (PKI) for a set of hardware, software, people, policies, and procedures needed to create, manage, distribute, use, store, and revoke digital certificates. In cryptography, a PKI is an arrangement that binds public keys with respective user identities by means of a certificate authority (CA). The user identity must be unique within each CA domain. The binding is established through the registration and issuance process, which, depending on the level of assurance the binding has, may be carried out by software at a CA, or under human supervision.

More generally, security is a motivating factor for use of smartphones (i.e., the handheld device 250) and their interactions with miniature devices (e.g., smart pills 100) and with cloud services (such as, e.g., a remote testing server 405 connected to a laboratory 450). Remote access to enterprise cloud services (as well as non-enterprise cloud services) is a challenge from a security point of view. However, one of the features of the present disclosure is the ability to embed security information such as an encryption key and password in the handheld device 250 that is carried by the user (and/or patient 402). This enables the user to provide secured login service for interaction with the handheld device 250 and remote databases 465 in the remote testing server 405.

FIG. 3 illustrates further details of the onboard testing unit 20 of the smart pill 100 according to an embodiment. The controller 10 may include various different sensors 305 for taking gathering data and taking measurements inside the body of the patients. The sensors 305 are miniature devices for temperature, pressure, imaging (i.e., pictures), and pH.

A tissue and fluid sample device 315 may extract a tissue sample and/or fluid sample of the patient while the smart pill 100 is in the patient's body. The tissue/fluid sample may be used for testing by the onboard testing unit 20. A DNA sequencing solid state nanopore device 310 may utilize the tissue/fluid sample for DNA sequencing and/or other genetic test while the smart pill 100 is in the body of the patient. The resulting test data is companion diagnostic data 220 that is passed and/or pulled from the onboard testing unit 20 (via the bus 65) to the controller 10. Based on the companion diagnostic data 220 received by the controller 10, the controller 10 can determine whether or not (e.g., dispense no drugs A, B, C, and D) to dispense the components 30 in the patient, determine how much (dosage) of the components 30 to dispense, and/or determine what combination of components 30 to dispense (e.g., dispense drugs A and D but not drugs B and C).

FIG. 3 also illustrates a representation of dispensers 35A-35D each with their with own respective actuation device 320A-320D that can push/expel the respective components 30 (e.g., drugs A, B, C, and D) out of the biocompatible material 201 shell of the smart pill 100 and/or open the respective reservoirs 5A-5D. The actuation device 320 which generally represents each actuation device 320A-D may be a compressed spring that is controlled to be released by the controller 10 to dispense the components 30 and/or piezoelectric device such as crystalline materials that elongate to expel the respective components 30 when an electric current flows from the power supply 230 as controlled by the controller 10.

FIG. 4 illustrates an example of a smart pill system/network 400 according to an embodiment. The system 400 may include a patient 402 representing a human patient who has swallowed the smart pill 100.

The handheld device 250 may include companion diagnostic data 220 (which includes the particular patient category) that is transmitted to the smart pill 100. For example, the controller 10 may be communicatively coupled wirelessly (via wireless communication signal 245) to the handheld device 250 to receive the companion diagnostic data 220. The companion diagnostic data 220 of the handheld device 250 can be received externally via a network 410 (e.g., the Internet) from the remote testing server 405 of a remote laboratory 450. For example, companion diagnostics (i.e., tests) are performed at the laboratory 450 on samples taken from the patient 402, and the companion diagnostic data 220 (corresponding to a particular patient category for the patient 402) is loaded onto the remote testing server 405 for transmission to the handheld device 250.

Additionally, the onboard testing unit 20 can directly provide the companion diagnostic data 220 by collecting samples from the patient's or animal's body directly via the tissue and fluid sample device 315. The smart pill 100 may be located in multiple places in the patient 402, and the multiple smart pills are represented as smart pills 460A, 460B, 460C, 460D, 460E, and 460F. The smart pills 460A-F are identical to the smart pill 100, and all description of the smart pill 100 apply to the smart pills 460A-F.

The multiple smart pills 460A-F all collect companion diagnostic data 220 while in the body of the patient 402, and the smart pills 460A-F send their respective companion diagnostic data to the smart pill 100 to be collected and stored as companion diagnostic data 220. Additionally, the smart pills 460A-F can send their respective companion diagnostic data to the handheld device 250, which can collect all companion diagnostic data 220 to send to the smart pill 100. The handheld device 250 can monitor the time in which each smart pill 100 and 460A-F was swallowed to estimate the approximate location of each smart pill 100 and 460A-F within the body of the patient 402, which allows the handheld device 250 to discriminate each individual smart pill 100 and 460A-F from one another. Additionally, each smart pill 100 and 460A-F is configured with a different encoding scheme (by the encryption/decryption protocol 225) such that each smart pill 100 and 460A-F can be identified by their respective transmissions sent to the smart pill 100 and the handheld device 250.

By having the smart pills 460A-F (along with smart pill 100) in different parts of the body and all the smart pills 450A-F (along with smart pill 100) communicatively coupled to one another, communicatively coupled to the smart pill 100, and/or communicatively coupled to the handheld device 250, this allows the smart pills 460A-F (alone or) with the smart pill 100 create a pill area network.

The smart pill 100 (as well as the smart pill 460A-F) can determine whether or not to dispense their relative components 30 as discussed herein.

Unlike state of the art smart pills, the smart pill 100 described herein is targeted to a particular biomarker and/or set of biomarkers (as determined by the software application 215 for the given companion diagnostic data 220 of the particular patient category) in the individual patient 402, has the ability to release no drug based on test criteria expressed in the software application (logic) 215 (e.g., programmed by the programmable logical interface 240 of the handheld device 250), and thus allows the release of drugs (i.e., components 30) to be contingent upon those criteria (as determined to be met by the software application 215) typically used in creation of a companion diagnostic.

State of the art smart pills use internal testing and measurement devices to target the drug to a particular location of the body (e.g., a position in the digestive tract). However, this is different from the smart pill 100 which demonstrates that companion diagnostic coupled to smart pill 100 provides the patient 402 specific drug therapy relative to the patient 402.

Furthermore, the present disclosure provides for remote modification of the software application (logic) 215 by the handheld device 250: for drug trial management, for smart pill communication for the purpose of allowing diagnostic testing at a location (such as the remote laboratory 450) separate from drug release (such as the smart pill 100 in the patient 402), and for creation of a pill area network for more advanced, multi-site diagnostic biomarker testing.

By using the smart pill 100, three problem areas of 1) drug development, 2) regulation, and 3) marketing/advertising can each be addressed. In the problem area of drug development, studies and trials to determine drug effectiveness may be controlled more precisely and modifications to the protocols more easily implemented in order to respond to changing conditions and new information discovered during the study. For example, patients or animals taking the smart pill 100 may be studied over a shorter period of time with a particular drug (e.g., component 30) and based on initial responsiveness, the biomarker-drug-dose combination may be adjusted to target the most promising subpopulation and/or dosage combination (all of which can be done by reprogramming the software application 215). In addition, controls may be more completely blind by using the smart pill 100, in that only the provider of the program (software application 215) knows what experiments are being conducted, and based on the design, perform this function completely remote from the clinical setting. In addition, an experimental protocol of the software application 215 may be expressed in a computer program, with logical statements, formula, algorithms, etc., used to generate new smart pill programs (e.g., modify, change, and/or replace the current software application (logic) 215) on the fly given the results of the study (e.g., using software logic 605 in FIG. 6). In this way, no individual patient 402 need ever know who was administered which drug.

Regarding the problem area of regulation, in regulating drug approval and prescription together with companion diagnostics, regulators face challenges associated with drugs and companion diagnostics often being produced by different pharmaceutical companies. The diagnostic and drug effectiveness must therefore be evaluated both separately and together. In the case of the present invention, the drug (e.g., components 30) and companion diagnostic system (e.g., companion diagnostic data 220) is completely encapsulated and therefore (must) be regulated as a single entity, thus simplifying the regulatory problem and forcing drug companies to produce a single drug delivery device. Furthermore, as in the case a certain drug and the FDA's subsequent proscription of a companion diagnostic testing for a K-RAS gene mutation, this modification, given an appropriately pre-configured companion diagnostic, could be accomplished by a simple reprogramming of the software application (logic) 215 for smart pills 100 delivering these drugs (i.e., components 30).

Regarding the problem area of advertising and marketing, companion diagnostic-coupled smart pills 100 afford an opportunity to market and advertise a complete clinical solution to both doctors and patients. The software application (logic) 215, the diagnostic component (including the software application 215 determining whether to dispense the components 30 and determining the amount to dispense based on the companion diagnostic data 220 while the smart pill 100 itself is in the patient 402), and the combinations of drugs (such as the various combination of different drugs A, B, C, and D which may not include all drugs) in the pill's respective reservoirs 5A, 5B, 5C, and 5D may be sufficiently complex and thorough to provide access to a very large market simultaneously. The effectiveness of the solution (the particular drug and/or combination of drugs in the smart pill 100) as a whole on a variety of diseases and conditions may be communicated based on results from the larger population. Furthermore, the complexities of the drug-diagnostic combinations can be hidden, since the drug combinations based on particular companion diagnostic may not be comprehensible to their specific markets, and instead a broader set of statistics and results may be communicated.

As discussed herein, the smart pill 100 makes use of companion diagnostics (i.e., tests) data 220 that provide information about the patient's genetic and genomic characteristics. This information (companion diagnostic data 220 for the determined patient category) is then used to make therapeutic treatment decisions (by the controller 10) for personalizing medicine and streamlining drug development. As mentioned, if drug approval is modified through time, this approach enables programming (e.g., criteria to determine subpopulation, dosage changes, etc.) of the software application (logic) 215. The smart pill area network (of the smart pill 100 and the smart pills 460A-F) allows communication between the smart pills to decide on criteria, etc.

Figure 5:
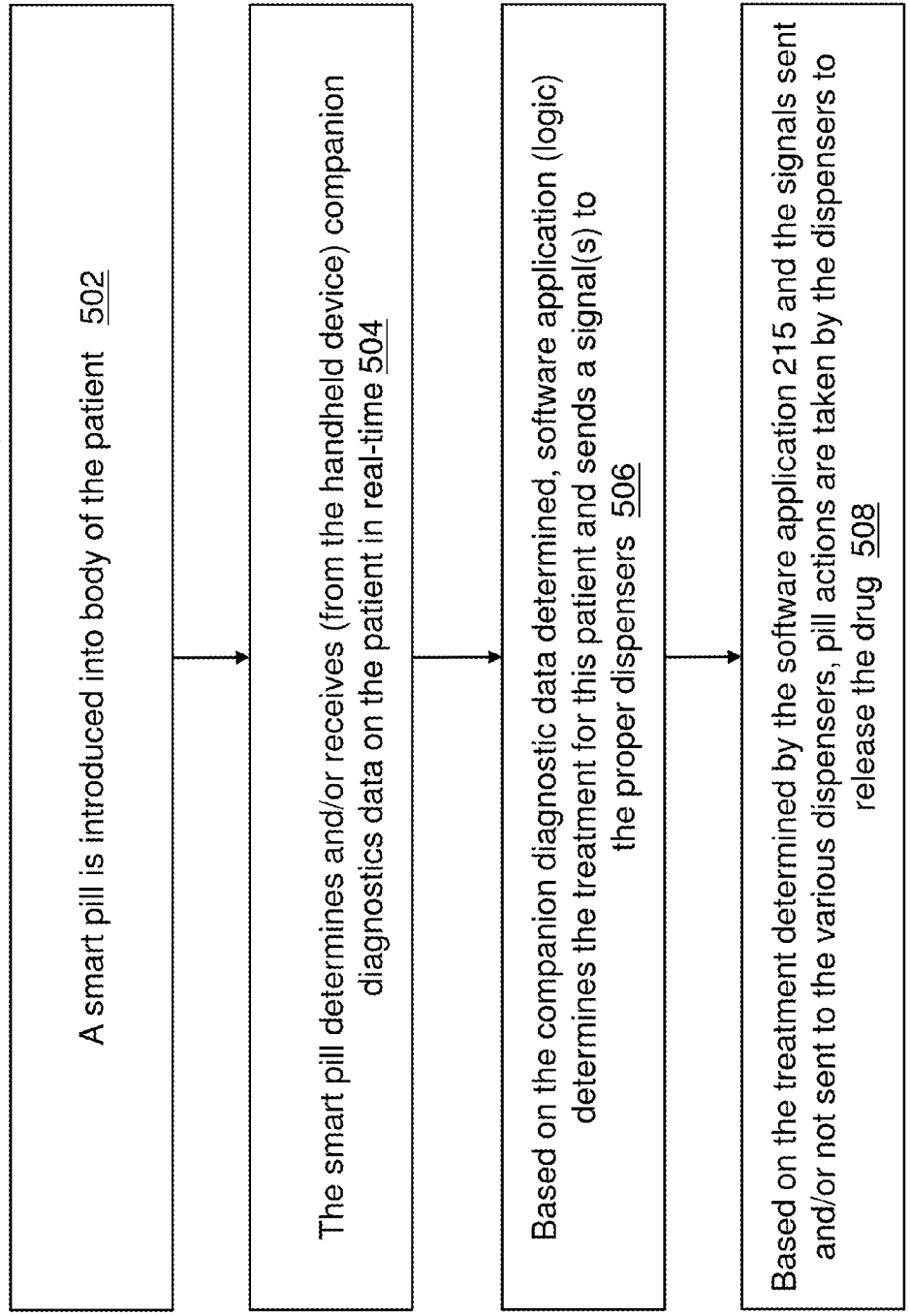
FIG. 5 is a flow chart of a method for using the smart pill along with a network of smart pills according to an embodiment.

FIG. 5 is a flow chart of a method 500 for using the smart pill 100 (along with the network of smart pills 460A-F) according to an embodiment.

The smart pill 100 is introduced into body of the patient 402 (other smart pill 460A-F may be introduced over time) at block 502. The smart pill 100 determines and/or receives from the handheld device 250 (medical) information (e.g., companion diagnostics data 220) on the patient 402 in real-time (e.g., relevant genetics) at block 504. Based on the companion diagnostic data 220 determined in block 504, the software application (logic) 215 determines the treatment for this patient 402 and sends a signal(s) to the proper dispensers 35A, 35B, 35C, and 35D at block 506.

Based on the treatment determined by the software application 215 and the signals sent (or not sent) to the various dispensers 35A, 35B, 35C, and/or 35D, pill actions are taken by the dispensers 35A, 35B, 35C, and/or 35D to release the drug at block 508. If no signals are sent (as determined by the software application 215) to release the drug, no dispensers 35 release the drugs. The drugs (components 30) released by the dispensers 35 may include nanoparticles, and the drugs can be released in micro-origami which is discussed further herein.

The smart pill 100 may be introduced into the digestive system. Additionally and/or alternatively, pill-like objects (which can be referred to as other smart pills 100 and/or smart pills 460A-F) can be introduced by other means (such as injection via a syringe, by hand, by surgery and/or other conventional techniques) into the blood stream, into body cavities, into joints, into organs, etc.

The medical information (i.e., companion diagnostic data 220) can be genetic (e.g., related to chromosome information, genetic sequence, the presence of genes, oncogenes, epigenetic markers, etc.). Note, as an example, that BRCA is a human tumor suppressor gene that produces a protein. BRCA1 is expressed in the cells of breast tissue, where it helps repair damaged DNA, or destroy cells if DNA cannot be repaired. If BRCA1 itself is damaged, damaged DNA is not repaired properly and this increases risks for cancers. In this example, genetic testing is performed on a sample (e.g., blood sample, tissue sample, saliva sample, and/or any type of fluid extracted from the patient 402) of the patient which may be performed at the laboratory 450 (shown in FIG. 4), and the BRCA1 gene sequence is determined by the laboratory 450. This genetic information of the patient 402 is provided/stored in the database 465 of the remote testing server 405 for patient 402. The API 470 utilizes the genetic information of patient 402 as a key (i.e., query and/or search string) in the database 465 to match the genetic information of the patient 402 to a patient category of the patient categories 468. To determine the specific patient category 468 for the patient 402, the API 470 (the software application) relates (matches) the genetic information of the patient 402 to known sequences for populations of normal patients (with no cancer) and/or patients subject to various cancers (as delineated according to the different patient categories 468). Each patient category 468 (including the specific patient category determined by the API 470 for the patient 402) has its own corresponding companion diagnostic data 220, and the patient categories 468 in database 465 correspond to prescribed, approved, and otherwise regulated treatments for the components 30 being tested. The API 470 (software application) relays to the smart pill 100 (via handheld device 250) the appropriate treatment (i.e., the companion diagnostic data 220 having the individual patient category 468 as determined for the patient 402), and the smart pill 100 applies the specific treatment for the patient 402 (which may be to release one or more components 30, release a combination of different components 30, and/or release no components 30 based on the specific patient category 468 in the companion diagnostic data 220 for the patient 402).

As seen in FIG. 4, the database 465 includes patient categories 468, and the patient categories 468 may include different patient categories 1, 2, 3 though patient category N, where patient category N is the last patient category being tested. For each of the patient categories 468, there is a set of rules for treatment. The rules for treatment which are evaluated by the software application 215 (particularly software logic 605 in FIG. 6) may be revised, thus changing the behavior of the smart pill 100 indirectly via the rules. Each patient category 468 corresponds to a subpopulation that is based on predefined genetic information (which include, e.g., chromosome information, genetic sequence, the presence of genes, oncogenes, epigenetic markers, etc., as discussed herein), and by the API 470 matching the genetic information of the patient 402 to the genetic information corresponding to one of the patient categories 468, the patient 402 is identified with that specifically matched patient category (e.g., patient category 2). Each patient category is tied to a specific treatment for a specific subpopulation that has been approved to receive the desired components 30 (and/or not receive the components 30). For example, patient category 2 (which could be any patient category 468) is part of the specific companion diagnostic data 220 for the patient 402. The remote testing server 405 transmits the companion diagnostic data 220 with the patient category 2 to the handheld device 250 via the network 410, and the handheld device 250 transmits the companion diagnostic data 220 to the smart pill 100. The software application (logic) 215 processes the companion diagnostic data 220 for the patient category 2 to determine whether or not to release the components 30 (along with which particular components to release) as discussed herein.

To further explain, genetic testing performed on the patient 402 (e.g., by the laboratory 450) may extract DNA from a tissue such as blood, then sequence the DNA using specific flanking markers such that the BRCA1 gene sequence is determined and stored in digital form in the database 465. This genetic information is then analyzed to the API 470 (software application) which compares the gene sequence determined for patient 402 to sequences for the patient categories 468 in the database 465, looking for matches. A score is given (by the API) to the gene sequence (for the patient 402) for each entry in the database 465 based on the agreement between gene sequences corresponding to the different patient categories 468, and the highest score is noted. If this (highest) score exceeds a threshold (corresponding to one of the specific patient categories 468), the database entry is read for that patient category 468 (by the API), providing information about the population of patients (for patient category 2) in which patient 402 has been identified in, and specifically their various cancers. The API 470 relates the patient population data to other references in the database, and relates/identifies the patient category 2 to an approved treatment. The API 470 (software application) relays (by handheld device 25) to the smart pill 100 (via the companion diagnostic data 220) the appropriate treatment, which the smart pill 100 executes by releasing a specific drug dose. Note that if the genetic sequence (of the patient 402) does not exceed the required threshold score for sequence agreement, no treatment is prescribed (via the companion diagnostic data 220), and the smart pill 100 does not release a drug. Furthermore, the patient's data is logged for additional analysis by doctors, scientists, and/or regulatory agencies, as the patient 402 may represent a new category of patients.

In a clinical study, many different patients 402 can be given the same smart pill 100. However, based on genetic testing information of each patient 402, the API 470 determines the appropriate patient category 468 for each individual patient 402. Each smart pill 100 receives the particular companion diagnostic data 220 (via the respective handheld device 250) for the determined patient category 468 such that the appropriate components 30 are released and/or not released in the respective patient 402. As such, the doctors, patients 402, researches, etc., are all unaware of the components 30 released and not released in the patients 402 undergoing the clinical study to test the particular treatment of the components. During the study, the individual patients 402 may take a series of smart pills 100 over the course of the clinical study while being unaware if the components 30 are actually released or not released. This allows all of the patient categories 468 to swallow the smart pills 100, while each patient category 1-N has its own specific treatment of the components 30 (which may include no treatment for one or more patient categories 468). Also, during the clinical study, the software logic 605 can be changed/revised for a specific population (which corresponds to a specific patient category 468 (such as patient category 2)), which thus allows reprogramming of the smart pill 100 (or series of smart pills 100 taken).

The medical information (i.e., companion diagnostic data 220) may also be biochemical, including hormone levels, acidity/pH, etc. Also, the medical information (i.e., companion diagnostic data 220) can also be proteomic and/or based on gene expression.

The medical information (i.e., companion diagnostic data 220) may also be based on temperature, pressure, biometric information, pulse, etc. Further, the medical information may be modified by a remote testing element (such as the remote laboratory 450) that analyzes and transforms the data into a form that is usable by the controller 10, based on the program (software application (logic) 215) relayed by the programmable logical interface 240 of the handheld device 250).

Further, the information (i.e., companion diagnostic data 220) may include geospatial information, based on GPS coordinates relayed from the handheld device 250 (such as a smart phone) indicating probable exposure to a pathogen, risk factor, etc. The information (i.e., companion diagnostic data 220) may be derived from communicatively coupling to other companion diagnostic components (e.g., onboard testing units 20) in other patients 402, to determine proximity in space or social networks, and associated risk factors, etc.

The information (companion diagnostic data 220) may include visual information, such as visual information related to inflammation, coloration, fractal dimensions of tissues, the characteristics of blood vessel formations, the infiltration of blood, etc.

The following is a simplified scenario of using the smart pill 100. Assume that the smart pill 100 is swallowed by the patient 402. An on-board camera (e.g., the sensor 305) detects a lesion within the duodenum. This detection may be automated, for example, based on visual pattern-recognition routines (included in the software application 215) stored in the memory 210. A signal is sent by the controller 10 to the dispenser 35, and an amount (as determined by the software application 215) of proton-pump-inhibitor drug is released/dispensed from the reservoir 5.

In another scenario, the handheld device 250 monitors body characteristics (e.g., disease state information) of the patient 402 by connecting to a disease database 465. For example, an application programming interface 280 of the handheld device 250 retrieves the disease state information (which can be included in companion diagnostic data 220) for the patient 402 by connecting to and communicating with an application programming interface 470 of the remote testing server 405 via the network 410. The handheld device 250 then conveys the disease state information to a user (e.g., physician), and the handheld device 250 can change smart-pill characteristics (i.e., modify software modules/components of the software application 215 via one or more pieces of software logic 605) and energy use by the smart pill 100 to improve drug delivery, ensure safety, and ensure continued operation of the smart pill 100 based on the needs of the patient 402. The handheld device 250 also receives information on alternate treatments with useful healing characteristics.

As noted above, the smart pill 100 may refer to pill-like objects that may be introduced by various means into the blood stream, into body cavities, into the GI tract, into joints, into organs, etc. The miniaturization of genetic (and other diagnostic) tests is underway and publicly documented in the related art. For example, a Nucleic Acids Research paper, entitled "A miniature integrated device for automated multistep genetic assays" in Nucleic Acids Res. 2000 Jun. 15; 28(12): e60 by Rolfe C. Anderson, Xing Su, Gregory J. Bogdan, and Jeffery Fenton (which is herein incorporated by reference in its entirety), notes that the device is smaller than a credit card, can manipulate over 10 reagents in more than 60 sequential operations and was tested for the detection of mutations in a 1.6 kb region of the HIV genome from serum samples containing as few as 500 copies of the RNA. The elements in this device are readily linked into complex, flexible, and highly parallel analysis networks for high throughput sample preparation or, conversely, for low cost portable DNA analysis instruments in point-of-care medical diagnostics, environmental testing and defensive biological agent detection.

In another scenario, a physician (a user) holds her smartphone which comprises the features of the handheld device 250 near the patient 402 who has swallowed the smart pill 100. The display 255 on the handheld device 250 (i.e., smartphone) changes to a red color signifying a danger condition in the patient 402. The user then presses a button (on a keyboard 290 and/or touch screen display 255) on the handheld device 250 (smartphone) to improve drug delivery characteristics of the smart pill 100 (e.g., increase dosage amount, add an additional drug (e.g., cause both drugs A and B to be dispensed), and to also receive information on alternative treatments, which do not necessarily have to be available via the current smart pill 100 in use.

Further information regarding companion diagnostics (i.e., the companion diagnostics data 220 for the patient 402) is provided below. Also, the article entitled "Companion Diagnostics: Evolving FDA Regulation and Issues for Resolution" by Krista Hessler Carver (May 14, 2010) is herein incorporated by reference in its entirety.

Companion diagnostics are tests that provide information about a patient's genetic and genomic characteristics, and the genetic and genomic characteristics are then used to make therapeutic treatment decisions. Companion diagnostics hold great promise for "personalizing" medicine and streamlining drug development. Existing approval authorities for drugs, biologics, medical devices and combination products were not designed with these "pharmacogenomic" and "pharmacogenetic" 1 type tests in mind, however. Consequently, the appropriate premarket pathways and labeling requirements for companion diagnostics and their associated therapies are unclear and in need of development.

The United States Food and Drug Administration (FDA or the agency) has undertaken to clarify the regulatory framework for companion diagnostics and their related therapies through a concept paper and other statements. Nevertheless, the agency's efforts are in the early stages and the regulatory construct for these products remains ambiguous at this time. FDA's case-by-case regulation provides some glimpse into the agency's approach and the governing requirements.

The smart pill 100 is utilized in conjunction with companion diagnostics (i.e., companion diagnostic data 220 of the patient 402 for a specific patient category 468), and the software application (logic) 215 evaluates the companion diagnostics data 220 (which are based on companion diagnostics (test) related to the specific use of the drug and/or each of the drugs in the smart pill 100) to determine if any of the components 30 (e.g., drugs A, B, C, and/or D) should be released in the patient. Also, the software application 215 determines which components 30 (e.g., drugs C and D) should not be released in the patient 402 while drugs A and B can be released, all of which is based on evaluating the companion diagnostic data 220 specific to this patient 402. Also, note that the components 30 can be for a single drug, and the companion diagnostic data 220 is evaluated to determine if the single drug should be released in the patient 402.

Figure 6:
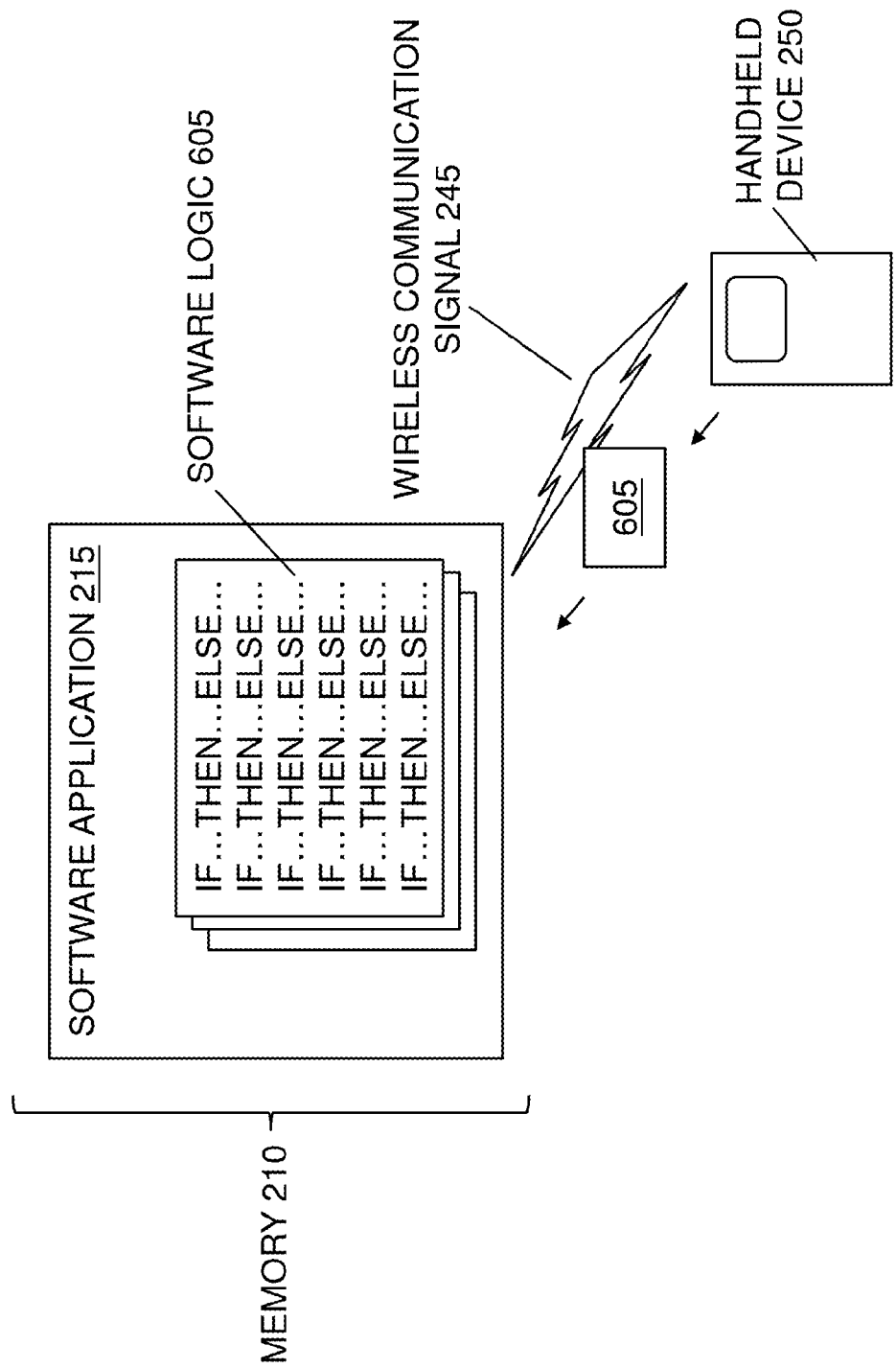
FIG. 6 illustrates details of a software application that runs accompanying software logic in the smart pill according to an embodiment.

As a way to meet federal regulations and/or as a way to ensure that a certain drug (i.e., component 30) is safe for a patient (such as the patient 402), companion diagnostics/tests (results which are specific to that drug) are run on the patient 402 (by the laboratory 450, and an accompanying software logic 605 specific to the particular drug (being tested and/or administered) is loaded in the memory 210 of the smart pill 100, as shown in FIG. 6. FIG. 6 illustrates further details of the software application 215, and shows that the accompanying software logic 605 is included in and run by the software application 215 for each of the drugs A, B, C, and D according to an embodiment. The software logic 605 (which is specifically designed to check that the components 30 are compatible for the patient 402 based on the companion diagnostics data 220 for the specific patient category 468) can be uploaded to smart pill 100 from the handheld device 250.

In one case, the software logic 605 is a series of logical evaluations performed on the companion diagnostics data 220 corresponding to the determined patient category 468 (by the software application 215), such as if "X" then "Y" else do "Z", if "J" then "K" else do "L", if not "H" then "I", and so forth. Once the software application 215 performs the software logic 605, the software application 215 makes a determination about dispensing the components 30 as discussed herein.

As one example of how the components 30 may be housed in respective reservoirs 5A, 5B, 5C, and 5D to be dispensed by the respective dispensers 35A, 35B, 35C, and 35D, the following discusses tiny packages as micro-origami which can be used to house the components 30.

Also, an article entitled "Micro-Origami—Tiny Packages for Drug Delivery" (May 30, 2008) by Roey Tzezana is herein incorporated by reference in its entirety. Researchers at the University of Southern California have demonstrated a way to manufacture miniscule containers that can be used to deliver precise micro or even nano quantities of drugs. The tiny containers are designed in a way that will enable delivering precise micro or even nano quantities of drugs, leading to better, safer treatment. The smart pill 100 can include these tiny containers to deliver components 30, such as drugs A, B, C, and D.

The container's size is less than 30 micro-meters, approximately half the width of a human hair. The new packages are manufactured in a two-step process: In the first step, flat patterns are created out of a sheet of polysilicon. These patterns are in essence origami-like. They resemble the fold-up shapes of paper pyramids, cubes, and other structures. The micro-origami, however, is 10,000 times smaller than the traditional Japanese art form. The basic patterns are etched into the polysilicon, and the area of the hinges is cleared to enable folding of the construct.

In the second step, the flat patterns are folded. The researchers electro-coat the blanks with permalloy to make them magnetic, leaving the hinge areas bare, to make sure the folding will occur only in those areas. Magnetic force is then applied to bend the hinges, followed by immersion of the tiny pieces in water. Capillary forces and pressure are generated by the water, and when the pieces dry off the final folding takes place, as the flaps closed over each other to form a closed shape. In a fashion similar to origami, the results can be varied by altering the sequence of folding, achieved by directing water at the polysilicon from different directions. By varying the drying, tighter seams can be produced, leading to packages that are closed more tightly, potentially allowing slower leakage of the drugs out of the containers.

This technique (i.e., micro-origami) for producing the micrometric packages is nicknamed voxels (volumetric pixels). The wide array of possible hinges and pattern geometries allow the creation of varied functional shapes, as well as smaller voxels. Many different shapes can be folder, including four—and five—sided pyramids, pentagonal 'lotus' shapes, and also simple square plates that folded over each other to create flat mini-envelopes. The technology is used by the smart pill 100 for drug delivery to the human body, by encapsulating the drug molecules (i.e., components 30) inside the tiny voxels.

Figure 7:
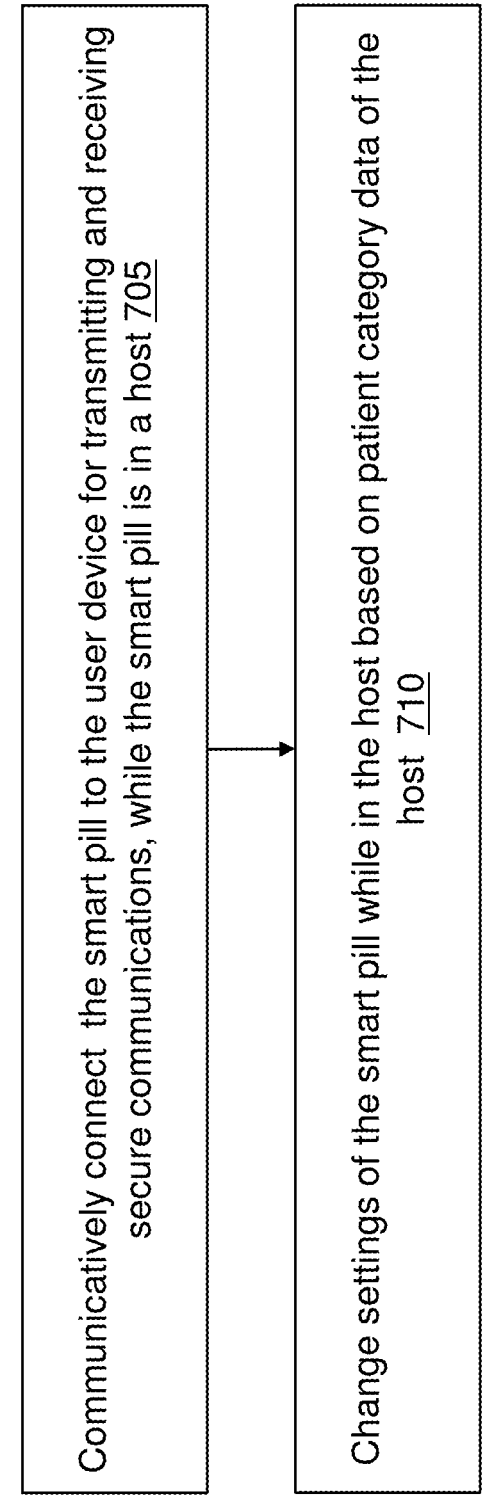
FIG. 7 is a flow chart of a method for the smart pill according to an embodiment.

Now turning to FIG. 7, a flow chart 700 of a method for the smart pill 100 is provided according to an embodiment.

The smart pill 100 is communicatively connected to the user device (e.g., handheld device 25) for transmitting and receiving secure communications, while the smart pill 100 is in a host (e.g., patient 402) at block 705.

As determined by the controller 10 (based on companion diagnostic data and/or a signal from the handheld device 250), the setting of the smart pill 100 can be automatically changed (by the software application 215) while in the host based on relayed patient category 468 data (i.e., companion diagnostic data 220) of the host, diagnostic data of the patient 402 collected by the onboard testing unit 20, and a relayed program (e.g., software logic 605) that takes patient category data and the diagnostic data as inputs at block 710. The setting relate to dispensing the components 30 in the patient 402 and energy usage.

The patient category 468 data of the host is provided to the smart pill 100 by the user device (i.e., handheld device 250). Based on the patient category 468 data of the host, the smart pill 100 is configured to at least one of determine that a drug should be dispensed in the host, determine that a drug should not be dispensed in the host, and determine that a combination of a plurality of drugs should be dispensed in the host. For example, the software application 215 can receive the companion diagnostic data 220 from the onboard testing unit 20 and/or from the handheld device 250. The software application 215 can evaluate the software logic 605 for the given companion diagnostic data 220, and determine to dispense the components 30, not to dispense (any or part) the components 30, and/or to dispense a specific combination of components 30 for the patient 402.

When determined (by the software application 215) that the drug should be dispensed, the smart pill 100 is configured to determine a dosage amount of the drug to dispense in the patient 402. Also, when determined (by the software application 215) that the plurality of drugs (e.g., drugs A, B, C, and/or D) should be dispensed, the smart pill 100 is configured to determine a dosage amount to individually dispense for each of the plurality of drugs. For example, extending the actuator device 320 by a predetermined distance (such as halfway) to expel components 30 corresponds to a certain dosage, and full extension corresponds to the maximum dosage for the respective component 30. Accordingly, each drug A, B, C, and D can have a different dosage corresponding to increments (e.g., 1-5, where 5 is maximum dosage and 1 is minimum dosage, with discrete dosage amount in between) for extending the respective actuation device 320A-D.

The smart pill 100 receives instructions from the user device (handheld device 250) to control energy usage of the smart pill 100. For example, the instructions received by the smart pill 100 may include decrease certain power cycles of the onboard testing unit 20, reduce transmission power for transmitting the wireless communication signal 245, etc. The features of the handheld device 250 can be implemented in at least one of a smartphone, a wristwatch, eyeglasses, and/or a personal digital assistant.

The medical report (e.g., showing companion diagnostic data 220) of the host is displayed on the user device (i.e., handheld device). The medical report (companion diagnostic data 220) of the patient 402 includes at least one of current medical information, past collected medical information for a predefined time interval, and/or a color (e.g., green means the patient 402 passed the companion diagnostics and can be given the components, while red means that the patient 402 is incompatible and no drugs should be released) that represents a summary of a medical state for the patient 402.

Multiple smart pills 100 can be in multiple hosts (e.g., multiple patients 402), and multiple handheld devices 250 respectively communicate with the smart pills 100, e.g., to pass along companion diagnostics data 220 collected by their respective onboard testing unit 20. The data signals received by the respective handheld devices 250 are automatically sent from the handheld devices 250 to a health database (e.g., database 465) that collects aggregate information on the multiple patients 402 respectively having their own smart pills 100. The data signals correspond to at least one of predefined disease states and smart pill efficacy of the plurality of smart pills 100 in the respective patients 402.

The smart pill 100 includes a controller (such as the controller 10) and a multiple dispensers (such as the dispensers 35A, 35B, 35C, and 35D) individually controlled by the controller 10. Based on the patient category 468 data (companion diagnostic data 220) of the patient 402, the controller 10 is configured to cause respective ones of the dispensers 35A, 35B, 35C, and/or 35D to respectively dispense (individually or simultaneously) multiple drugs in a specified combination.

Figure 8:
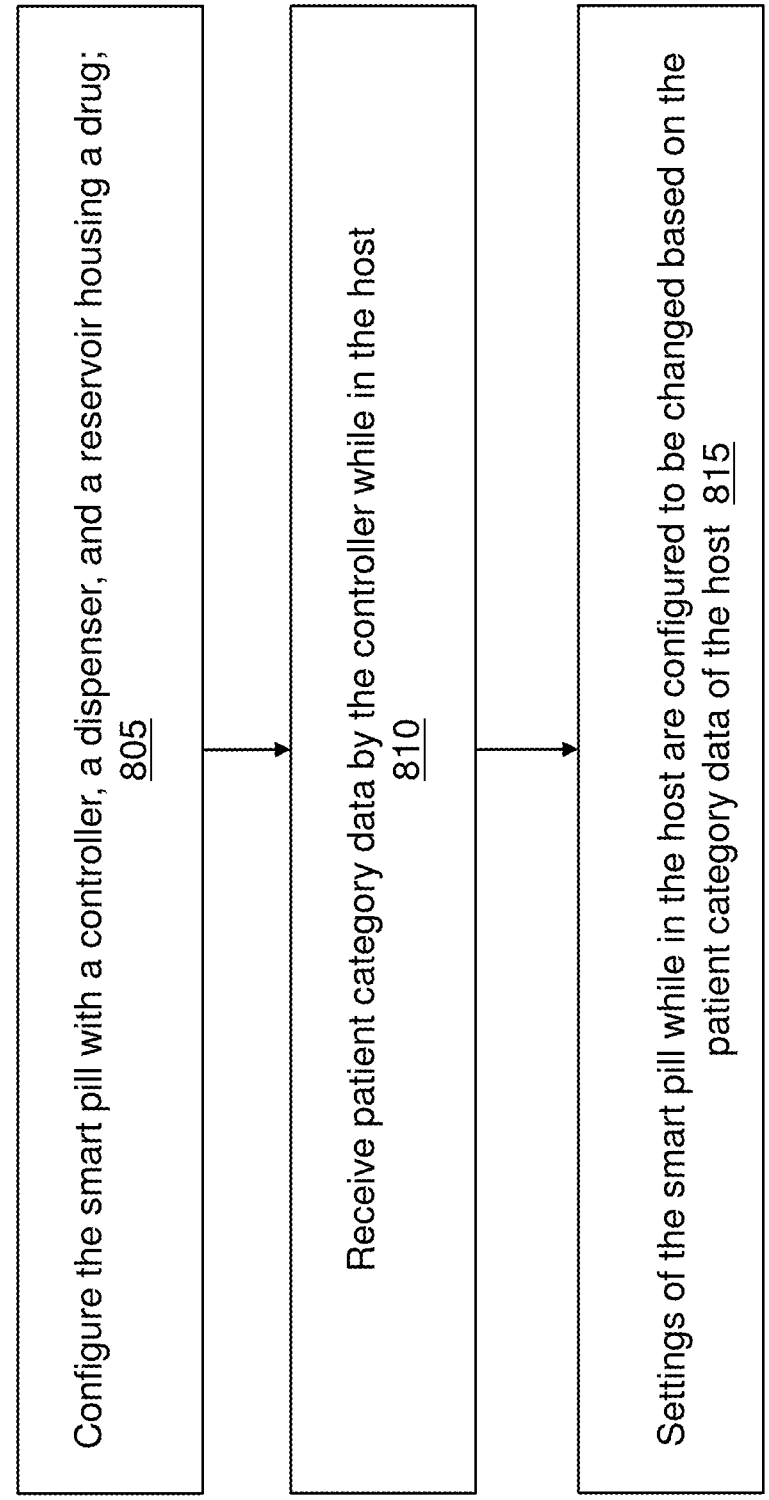
FIG. 8 is a flow chart of a method for the smart pill according to an embodiment.

FIG. 8 is a flow chart 800 of a method for the smart pill 100 configured to be swallowed by a patient 402 according to an embodiment.

The smart pill 100 is configured with a controller 10, a dispenser 35, and a reservoir 5 housing a drug (e.g., component 30) at block 805. The controller 10 is configured to receive the particular patient category 468 (e.g., patient category 2) at block 810. Settings of the smart pill 100 while in the host are configured to be automatically (by the software application 215) changed based on the relayed patient category 468 data of the patient 402, diagnostic data of the patient 402 collected by the smart pill 100, and a relayed program (e.g., software logic 605) that takes the patient category data and the diagnostic data as inputs at block 815.

Figure 9:
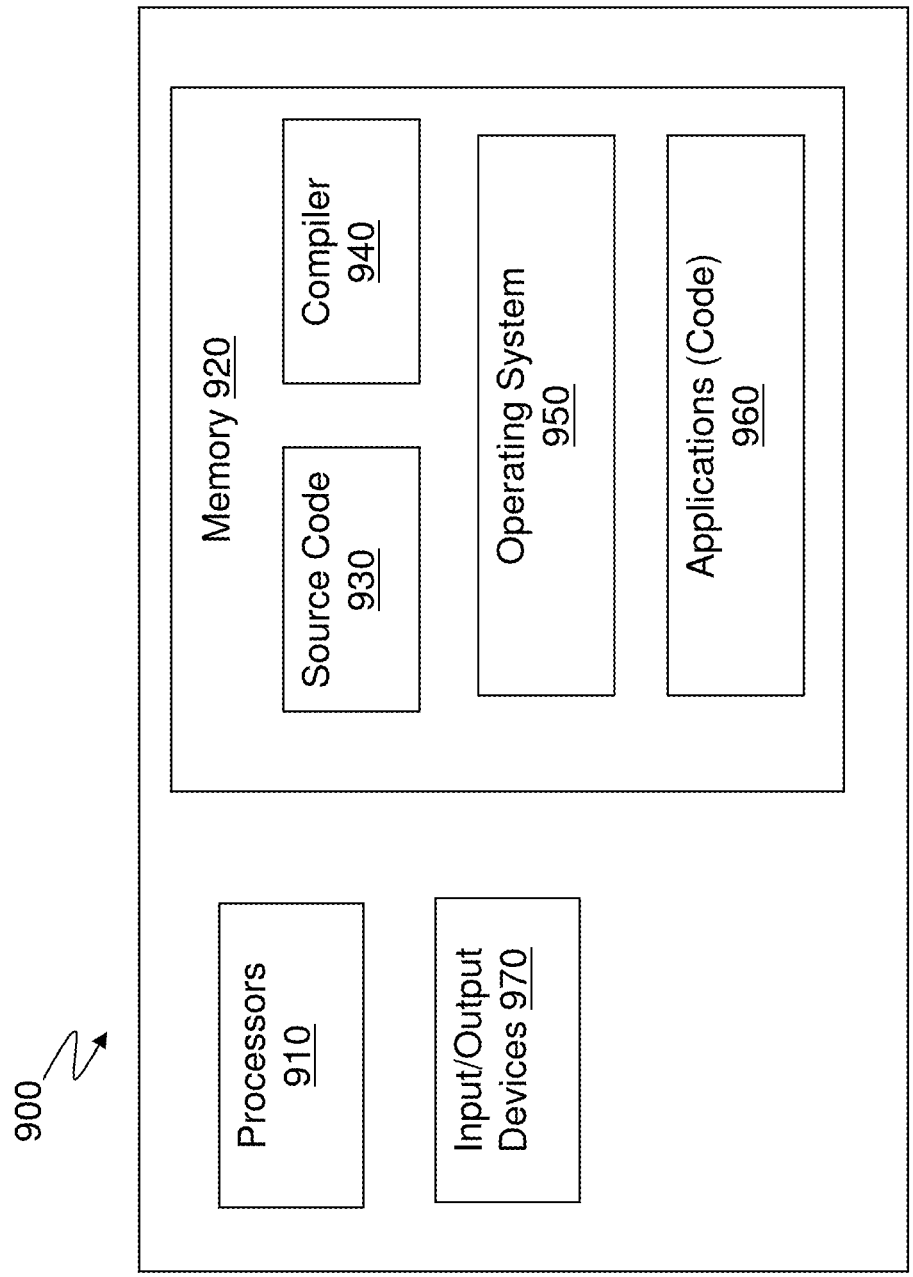
FIG. 9 illustrates an example of a computer having capabilities, which may be included in embodiments.

FIG. 9 illustrates an example of a computer 900 having capabilities, which may be included in exemplary embodiments. Various methods, procedures, modules, flow diagrams, tools, applications, circuits, elements, and techniques discussed herein may also incorporate and/or utilize the capabilities of the computer 900. Moreover, capabilities of the computer 900 may be utilized to implement features of exemplary embodiments discussed herein. One or more of the capabilities of the computer 900 may be utilized to implement, to connect to, and/or to support any element discussed herein (as understood by one skilled in the art) in FIGS. 1-8.

Generally, in terms of hardware architecture, the computer 900 may include one or more processors 910, computer readable storage memory 920, and one or more input and/or output (I/O) devices 970 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 910 is a hardware device for executing software that can be stored in the memory 920. The processor 910 can be virtually any custom made or commercially available processor, a central processing unit (CPU), a data signal processor (DSP), or an auxiliary processor among several processors associated with the computer 900, and the processor 910 may be a semiconductor based microprocessor (in the form of a microchip) or a macroprocessor.

The computer readable memory 920 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 920 may incorporate electronic, magnetic, optical, and/or other types of storage media. Note that the memory 920 can have a distributed architecture, where various components are situated remote from one another, but can be accessed by the processor 910.

The software in the computer readable memory 920 may include one or more separate programs, each of which comprises an ordered listing of executable instructions for implementing logical functions. The software in the memory 920 includes a suitable operating system (O/S) 950, compiler 940, source code 930, and one or more applications 960 of the exemplary embodiments. As illustrated, the application 960 comprises numerous functional components for implementing the features, processes, methods, functions, and operations of the exemplary embodiments. The application 960 of the computer 900 may represent numerous applications, agents, software components, modules, interfaces, controllers, etc., as discussed herein but the application 960 is not meant to be a limitation.

The operating system 950 may control the execution of other computer programs, and provides scheduling, input-output control, file and data management, memory management, and communication control and related services.

The application 960 may be a source program, executable program (object code), script, or any other entity comprising a set of instructions to be performed. When a source program, then the program is usually translated via a compiler (such as the compiler 940), assembler, interpreter, or the like, which may or may not be included within the memory 920, so as to operate properly in connection with the O/S 950. Furthermore, the application 960 can be written as (a) an object oriented programming language, which has classes of data and methods, or (b) a procedure programming language, which has routines, subroutines, and/or functions.

The I/O devices 970 may include input devices (or peripherals) such as, for example but not limited to, a mouse, keyboard, scanner, microphone, camera, etc. Furthermore, the I/O devices 970 may also include output devices (or peripherals), for example but not limited to, a printer, display, etc. Finally, the I/O devices 970 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 970 also include components for communicating over various networks, such as the Internet or an intranet. The I/O devices 970 may be connected to and/or communicate with the processor 910 utilizing Bluetooth connections and cables (via, e.g., Universal Serial Bus (USB) ports, serial ports, parallel ports, FireWire, HDMI (High-Definition Multimedia Interface), etc.).

When the computer 900 is in operation, the processor 910 is configured to execute software stored within the memory 920, to communicate data to and from the memory 920, and to generally control operations of the computer 900 pursuant to the software. The application 960 and the O/S 950 are read, in whole or in part, by the processor 910, perhaps buffered within the processor 910, and then executed.

When the application 960 is implemented in software it should be noted that the application 960 can be stored on virtually any computer readable storage medium for use by or in connection with any computer related system or method. In the context of this document, a computer readable storage medium may be an electronic, magnetic, optical, or other physical device or means that can contain or store a computer program for use by or in connection with a computer related system or method.

The application 960 can be embodied in any computer-readable medium 920 for use by or in connection with an instruction execution system, apparatus, server, or device, such as a computer-based system, processor-containing system, or other system that can fetch the instructions from the instruction execution system, apparatus, or device and execute the instructions. In the context of this document, a "computer-readable storage medium" can be any means that can store, read, write, communicate, or transport the program for use by or in connection with the instruction execution system, apparatus, or device. The computer readable medium can be, for example but not limited to, an electronic, magnetic, optical, or semiconductor system, apparatus, or device.

More specific examples (a nonexhaustive list) of the computer-readable medium 920 would include the following: an electrical connection (electronic) having one or more wires, a portable computer diskette (magnetic or optical), a random access memory (RAM) (electronic), a read-only memory (ROM) (electronic), an erasable programmable read-only memory (EPROM, EEPROM, or Flash memory) (electronic), an optical fiber (optical), and a portable compact disc memory (CDROM, CD R/W) (optical).

In exemplary embodiments, where the application 960 is implemented in hardware, the application 960 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It is understood that the computer 900 includes non-limiting examples of software and hardware components that may be included in various devices, servers, and systems discussed herein, and it is understood that additional software and hardware components may be included in the various devices and systems discussed in exemplary embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or schematic diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As described above, embodiments can be embodied in the form of computer-implemented processes and apparatuses for practicing those processes. In embodiments, the invention is embodied in computer program code executed by one or more network elements. Embodiments include a computer program product on a computer usable medium with computer program code logic containing instructions embodied in tangible media as an article of manufacture. Exemplary articles of manufacture for computer usable medium may include floppy diskettes, CD-ROMs, hard drives, universal serial bus (USB) flash drives, or any other computer-readable storage medium, wherein, when the computer program code logic is loaded into and executed by a computer, the computer becomes an apparatus for practicing the invention. Embodiments include computer program code logic, for example, whether stored in a storage medium, loaded into and/or executed by a computer, or transmitted over some transmission medium, such as over electrical wiring or cabling, through fiber optics, or via electromagnetic radiation, wherein, when the computer program code logic is loaded into and executed by a computer, the computer becomes an apparatus for practicing the invention. When implemented on a general-purpose microprocessor, the computer program code logic segments configure the microprocessor to create specific logic circuits.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A smart pill system, comprising:
   a user device; and
   a smart pill configured to be swallowed by a host in a clinical study executed by an application program interface (API) of a remote testing server, the smart pill communicatively connected to the user device for transmitting and receiving secure communications including companion diagnostic data of the host;
   wherein the smart pill comprises a controller swallowable in the smart pill;
   a plurality of smart pills configured to be swallowed by a plurality of hosts in the clinical study executed by the API of the remote testing server;
   wherein each of the plurality of smart pills and the smart pill comprises drugs being tested on the plurality of different hosts in the clinical study;
   another controller in each of the plurality of smart pills, the another controller and the controller configured to control release of the drugs, the another controller configured to be in communication with the API of the remote testing server;
   wherein a release and a non-release of the drugs in the plurality of smart pills and the smart pill are blind and are controlled by the API of the remote testing server, the release and the non-release being blind is defined as no humans including a doctor and the plurality of hosts being unaware of which of the plurality of hosts have swallowed the plurality of smart pills that release and do not release the drugs, such that none of the plurality of hosts knows whether the drugs are administered or not;

wherein the release and the non-release of the drugs in the plurality of smart pills and the smart pill are controlled according to patient categories in a database, wherein the patient categories comprise predefined genetic information, such that the host and the plurality of hosts are matched to the patient categories;

wherein the another controller and the controller, of the plurality of smart pills and the smart pill for a subpopulation of the plurality of hosts, is configured to be modified via the API given results of the clinical study, the another controller and the controller being modified to target the release of the drugs for the subpopulation according to the patient categories of the remote testing server, the subpopulation being defined as one of the patient categories in a database of the remote testing server;

wherein the smart pill comprises:
separate reservoirs configured to separately house three or more drugs, the smart pill having a longitudinal direction such that a first reservoir containing a first one of the three or more drugs and a second reservoir containing a second one of the three or more drugs are on an opposite side of the smart pill in the longitudinal direction from a third reservoir containing a third one of the three or more drugs, the first, second, and third reservoirs occupying longitudinal ends of the smart pill;

a plurality of dispensers individually controlled by the controller in which a first dispenser is directly adjacent to the first reservoir and is configured to expel the first one of the three or more drugs through a biocompatible shell, a second dispenser is directly adjacent to the second reservoir and is configured to expel the second one of the three or more drugs through the biocompatible shell, and a third dispenser is directly adjacent to the third reservoir and is configured to expel the third one of the three or more drugs through the biocompatible shell;

the first and second dispensers configured to expel the first one and the second one of the three or more drugs out of the first and second reservoirs at one longitudinal end of the smart pill, the third dispenser configured to expel the third one of the three or more drugs out of the third reservoir at another longitudinal end of the smart pill opposite the one longitudinal end, wherein the first dispenser, the second dispenser, and the third dispenser are each a spring, wherein the spring is configured to be extended a first increment through a last increment in order to expel the first one, the second one, and the third one of the three or more drugs into the host, wherein the first increment is a minimum dosage amount and the last increment is a maximum dosage amount to individually expel the first one, the second one, and the third one of the three or more drugs into the host;

a first bus connecting the first dispenser to the controller, a second bus connecting the second dispenser to the controller, and a third bus connecting the third dispenser to the controller;

wherein the combination of the three or more drugs that are to be dispensed in the host include options of: dispensing no drugs of the three or more drugs, and dispensing a specific combination of the three or more drugs without dispensing some drugs.

2. The system of claim 1, wherein the controller is configured to utilize the companion diagnostic data of the host to determine a combination of the three or more drugs that are to be dispensed in the host;
wherein the controller is configured to dispense the combination of the three or more drugs in the host according to the companion diagnostic data of the host;
wherein the companion diagnostic data corresponds to test results of the host, the test results comprising genetic results, proteomic results, and gene expression tests results.

3. The system of claim 2, wherein when determined that a drug of the three or more drugs is to be dispensed, the smart pill is configured to determine a dosage amount of the drug of the three or more drugs to dispense in the host.

4. The system of claim 2, wherein the three or more drugs at least comprise drug A, drug B, and drug C; and
wherein the plurality of dispensers are piezoelectric devices.

5. The system of claim 1, wherein the smart pill receives instructions from the user device to control energy usage of the smart pill.

6. The system of claim 1, wherein the smart pill further comprises an onboard testing unit comprising a tissue and fluid sampler device, the controller and onboard testing unit positioned in a middle portion of the smart pill.

7. The system of claim 6, wherein the user device is eyeglasses.

8. The system of claim 1, wherein a medical report of the host is displayed on the user device;
wherein the medical report of the host comprises current medical information, and past collected medical information for a predefined time interval.

9. The system of claim 2, wherein based on the companion diagnostic data of the host, the controller is configured to cause respective ones of the plurality of dispensers to dispense multiple drugs of the three or more drugs in a specified combination.

10. The system of claim 1, wherein the smart pill is configured to release at least one of stem cells, viruses, parasite eggs, parasites, and bacteria;
further comprising: a plurality of smart pills configured to be swallowed by the host such that the plurality of smart pills and the smart pill form a pill network in the host, the plurality of smart pills being configured to house the three or more drugs, wherein the plurality of smart pills and the smart pill are configured to communicate with one another separate from the user device, wherein each of the plurality of smart pills and the smart pill is configured with a different encryption and decryption protocol such that each of the plurality of smart pills and the smart pill is separately identifiable.

11. The system of claim 1, wherein in response to a user holding the user device in proximity to the host having swallowed the smart pill, the user device displays a danger condition such that the user selects an option on the user device to improve drug delivery characteristics of the smart pill.

* * * * *